United States Patent [19]

O'Brien

[11] Patent Number: 5,242,305
[45] Date of Patent: Sep. 7, 1993

[54] METHOD AND COMPOSITION FOR REMOVING MERCURY VAPOR FROM DENTAL RESTORATIONS

[76] Inventor: William J. O'Brien, 1320 Morningside, Ann Arbor, Mich. 48103

[21] Appl. No.: 861,773

[22] Filed: Apr. 2, 1992

[51] Int. Cl.$^5$ ............................ A61C 5/00; C22C 5/08
[52] U.S. Cl. ................................ 433/228.1; 420/502; 420/503
[58] Field of Search ...................... 433/226, 227, 228.1; 420/502, 503

[56] References Cited

U.S. PATENT DOCUMENTS

| | | | |
|---|---|---|---|
| 4,064,629 | 12/1977 | Stoner et al. | 433/226 X |
| 4,385,892 | 5/1983 | Sato et al. | 433/226 X |
| 4,427,501 | 1/1984 | Rogers | 433/228.1 X |
| 4,659,384 | 4/1987 | Daigo et al. | 433/228.1 X |
| 4,664,629 | 5/1987 | Chodkowski | 433/228.1 |
| 5,076,789 | 12/1991 | Tanaka | 433/227 X |
| 5,106,303 | 4/1992 | Oden et al. | 433/226 X |

Primary Examiner—Gene Mancene
Assistant Examiner—Nicholas D. Lucchesi
Attorney, Agent, or Firm—Rohm & Monsanto

[57] ABSTRACT

The amount of mercury released from amalgam restorations in the teeth of living beings is significantly reduced without changing the composition of the silver-tin-copper alloy or changing the mercury-alloy ratio. This is achieved by introducing a mercury-absorbing metal component which acts only during the final setting stage of the amalgam. In a process embodiment, this is achieved by introducing a mercury-absorbing metal component which is applied to the prepared tooth cavity walls where it absorbs excess mercury from the setting amalgam. In a composition embodiment, the composition of the amalgam restoration consists of three components: a finely divided silver-tin-copper alloy; mercury; and a mercury-absorbing metal powder containing at least 50% by weight of palladium and the remainder of the group consisting of gold, copper, platinum, indium, zinc, and silver, some of which may be present as a coating on the palladium base powder. The palladium-containing component efficiently alloys with the excess mercury from the restoration thereby reducing the mercury vapor released into the patient's mouth.

15 Claims, 1 Drawing Sheet

METHOD AND COMPOSITION FOR REMOVING MERCURY VAPOR FROM DENTAL RESTORATIONS

BACKGROUND OF THE INVENTION

This invention relates generally to dental restorations, and in particular, to methods and compositions for use in the restoration of the teeth of living beings while reducing the emission of mercury vapors from the restorations into the mouths of the patients.

Amalgam restoration compounds which are in widespread use are generally formed of silver-tin-copper alloys, and contain approximately 40% to 50% by weight of mercury. Although such metal compositions produce good mechanical results, they have been found to release toxic mercury vapor into the mouths of patients.

One prior art effort at reducing the amount of mercury vapor which is emitted from the amalgam includes reducing the proportion of mercury in the mercury-silver alloy, and adding other elements to the silver alloy. Neither of these approaches has proved to be successful because they adversely affect the working qualities and mechanical properties of the resulting amalgam used to form the restoration.

It is, therefore, an object of this invention to provide an amalgam composition which is possessed of acceptable mechanical properties when used in dental restorations, and which does not release mercury vapor into the mouth of a patient.

It is another object of this invention to provide a method of effecting a dental restoration which eliminates or greatly reduces mercury vapor in the mouth of the patient.

It is also an object of this invention to provide a system for effecting dental restorations which permits conventional dental techniques and tools to be used, and which does not require special equipment.

It is a further object of this invention to provide a simple and inexpensive system for reducing or eliminating the release of mercury vapor into the mouth of a patient following a dental restoration.

SUMMARY OF THE INVENTION

The foregoing and other objects are achieved by this invention which provides, in a composition aspect thereof, a dental amalgam formed of approximately between 40% and 60% by weight of a silver based powder containing approximately between 1% and 27% by weight of copper. Approximately between 1% and 10% by weight of the dental amalgam is a palladium based powder, and approximately between 40% and 60% by weight of the amalgam is mercury.

In one embodiment of the invention, the palladium based powder is finally divided to a particle size of approximately between 0.25 $\mu$m and 0.55 $\mu$m. The palladium based powder, in certain embodiments, may consist substantially of pure palladium. However, in other embodiments, the palladium based powder may contain at least 50% by weight of palladium.

In embodiments of the invention where the palladium based powder is not substantially pure palladium, the remaining portion over the palladium may consist of a combination of copper, silver, gold, platinum, zinc, and/or indium.

The dental amalgam composition of the present invention may contain palladium based powder in the form of an alloy which consists of at least 50% by weight of palladium. The palladium is alloyed with a selectable combination of copper, silver, gold, platinum, zinc, and indium.

In accordance with a method aspect of the invention, the method includes the steps of installing a mercury-absorbing metal composition in the dental region to be restored, and then installing an amalgam mix containing mercury in the dental region to be restored, whereby mercury which is released from the amalgam mix binds to the mercury-absorbing metal composition.

In some embodiments of this method aspect of the invention, the amalgam mix may be comprised of a mixture of a silver alloy-mercury plastic amalgam mix. The mercury-absorbing metal composition contains at least approximately 50% by weight of palladium, and the remainder is, as previously stated, a combination of gold, copper, platinum, indium, zinc, and gold.

In the practice of the method aspect of the invention, the mercury-absorbing metal composition is in the form of a metal powder having a particle size of approximately between 0.1 $\mu$m and 50 $\mu$m. Alternatively, this composition may be in the form of a metal foil having a thickness of approximately between 5 $\mu$m and 13 $\mu$m.

In accordance with a further method aspect of the invention, a method of restoring a dental region in a living being contains the steps of preparing a cavity region in the dental region to be restored, installing a mercury-absorbing metal composition in the cavity region, this composition containing palladium, and then installing the amalgam mix containing mercury in the cavity region, whereby mercury released from the amalgam mix binds to the mercury-absorbing metal composition.

In the practice of this method aspect of the invention, the steps of installing the mercury-absorbing metal composition may include the step of lining at least a portion of the cavity region with the mercury-absorbing metal composition. Such a lining may be in the form of a thin foil which, as previously indicated, is formed of palladium in combination with other metals selected from the group of gold, platinum, silver, and indium. Alternatively, the mercury-absorbing composition may be in the form of a powder of palladium in combination with the other metals, and having the particle size of approximately between 0.25 $\mu$m and 0.55 $\mu$m.

The present invention reduces the amount of mercury released from the amalgam restoration without changing the composition of the silver-tin-copper alloy or changing the mercury-alloy ratio. This, as previously stated, is achieved by introducing a mercury-absorbing metal component which is applied to the prepared tooth cavity walls where it absorbs excess mercury from the setting amalgam. The composition of the amalgam restoration of this invention consists of three components:

(a) A finely divided silver-tin-copper alloy;
  (b) A mercury-absorbing metal powder containing at least 50% by weight of palladium and the remainder of the group consisting of gold, copper, platinum, indium, zinc, and silver; and
  (c) Approximately 40% to 60% by weight of mercury.

Contrary to prior belief, palladium has a greater affinity for absorbing mercury than gold. Accordingly, in the preferred embodiment of this invention, a palladium based composition is used to line the patient's prepared tooth cavity prior to condensation of the silver alloy-mercury base by a dentist. Although the working qualities of the amalgam are not changed during handling, the palladium containing component efficiently alloys with any excess mercury from the restoration thereby reducing the mercury vapor released into the patient's mouth by a factor of 10, as measured with a Jerome 511 mercury analyzer. In addition, amalgam restorations made in accordance with the present invention release less than 25 times the amount released upon polishing a conventional amalgam restoration.

In accordance with the invention, the palladium based mercury-absorbing component contains at least 50% by weight of palladium and the remainder of the group consisting of gold, platinum, copper, silver, and indium. The palladium based mercury-absorbing component may be in the form of a thin foil or preferably a fine powder with a particle size of approximately between 0.25 and 0.55 μm. The palladium base may be an alloy or mixture with elements from the group consisting of gold, platinum, copper, silver, or indium. Pure palladium has the greatest capacity to absorb mercury, but alloying or mixing with base metal lowers the cost and improves working properties. In addition, palladium provides the particular advantage of being characterized with excellent biocompatibility.

In an alternative embodiment of the invention, the mercury-absorbing palladium base component is coated, such as by being plated, with a thin layer of copper, silver, tin, gold, zinc, or indium composition. This coated mercury-absorbing palladium component powder is then mixed with the conventional silver-tin-copper alloy and mercury, and condensed into the prepared tooth cavity. At that time, the outer plating is dissolved in mercury or penetrated by mercury, and the palladium component absorbs excess mercury.

It is an advantage of this embodiment that the step of coating the tooth component with the mercury-absorbing component is eliminated. Also, the palladium component may be premixed with silver alloy by the manufacturer, and the dentist carries out the final step of mixing with mercury.

In order to prevent leakage around the amalgam restoration and to protect the pulp of the teeth from chemical and physical irritation, varnishes and cement liners are often used to line the surfaces of prepared cavities before placement of the amalgam restoration. The same varnishes and cement liners may be used with the method of this invention. The palladium-absorbing component is applied to the surface of the varnish or cement layer where it will come in contact with the silver alloy-mercury paste upon condensing into the prepared cavity. Another method of this invention is the incorporation of the palladium based component into conventional varnishes and cement lining materials before lining the prepared cavity. Coating the palladium based metal powder with a stearic acid layer before incorporation into a varnish or cement aids in the absorption of mercury.

BRIEF DESCRIPTION OF THE DRAWING

Comprehension of the invention is facilitated by reading the following detailed description, in conjunction with the annexed drawing, in which.

DETAILED DESCRIPTION

Figure 1:
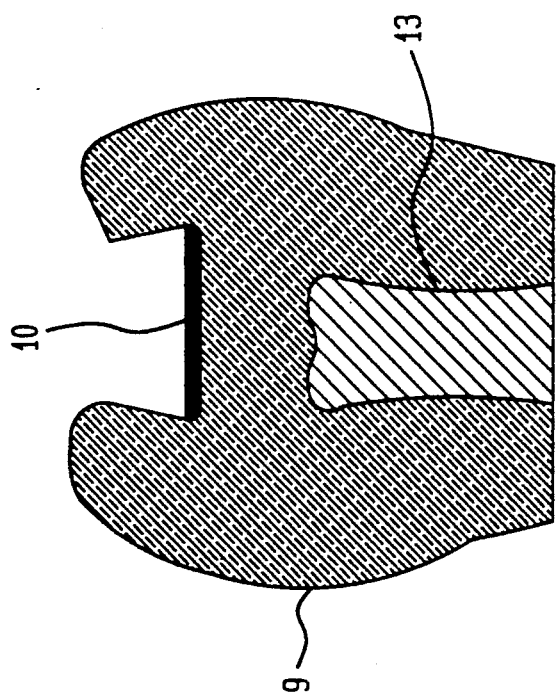
FIG. 1 is a cross-sectional side view of the crown of a posterior tooth with a prepared Type I cavity lined with the palladium based mercury-absorbing component.

FIG. 1 is a cross-sectional side view of a posterior tooth 9. The posterior tooth is shown to have a Type I cavity prepared at the top thereof, and a mercury-absorbing type component 10 is shown lining the bottom of the cavity. In accordance with the invention, the mercury-absorbing component is a palladium based material which may be combined with other metals. Reference numeral 13 designates the pulp of tooth 9.

Figure 2:
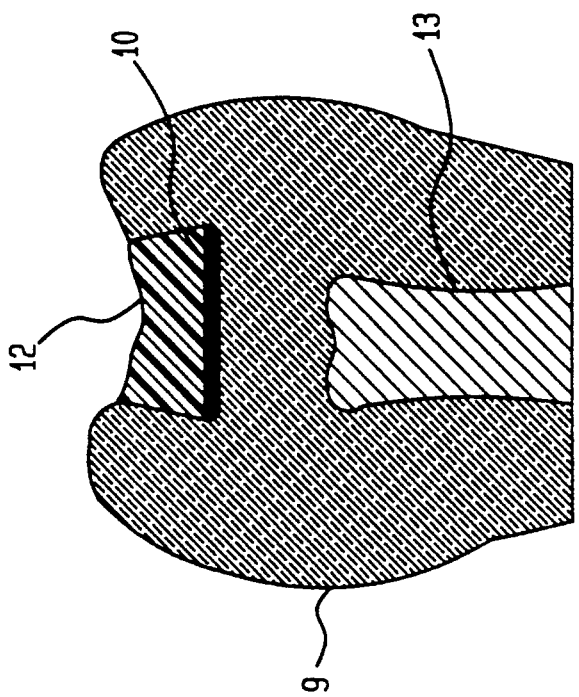
FIG. 2 is a cross-sectional view of the tooth of FIG. 1 with the amalgam restoration completed in accordance with the invention.

FIG. 2 is a cross-sectional representation of tooth 9 of FIG. 1, and accordingly correspondingly analogous elements of structure are similarly designated. As shown, an amalgam restoration 12 is arranged to overlie mercury-absorbing component 10 in the cavity region. Amalgam restoration 12 is made by combining a silver-tin-copper alloy with mercury and condensing same into the prepared cavity region. Mercury vapors (not shown) which are released by the amalgam will bind to the mercury-absorbing component, thereby significantly reducing the amount of mercury vapor which is released into the mouth of a patient (not shown).

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A dental amalgam composition comprising:
   approximately between 40% and 60% by weight of silver base powder containing approximately between 1% and 27% by weight of copper;
   approximately between 1% and 10% by weight of a palladium base powder said palladium base powder being in the form of an alloy consisting of at least 50% by weight of palladium, said palladium base powder being coated with a metal from the group consisting of copper, silver, gold, platinum, zinc, and indium; and
   approximately between 40% and 60% by weight of mercury.

2. The dental amalgam composition of claim 1 wherein said palladium base powder is divided to a particle size of approximately between 0.25 μm and 0.55 μm.

3. The dental amalgam composition of claim 1 wherein said palladium base powder consists substantially of pure palladium.

4. The dental amalgam composition of claim 1 wherein said palladium base powder comprises at least 50% by weight of palladium.

5. The dental amalgam composition of claim 4 wherein the remaining portion of said palladium base powder is comprised from the group consisting of copper, silver, gold, platinum, zinc, and indium.

6. The dental amalgam composition of claim 1 wherein said palladium base powder comprises an alloy consisting of at least 50% by weight of palladium, and the remainder from the group consisting of copper, silver, gold, platinum, zinc, and indium.

7. A method of preparing a dental amalgam restoration in a dental region to be restored, the method comprising the steps of:
- first installing a mercury-absorbing palladium composition in the dental region to be restored; and
- second installing an amalgam mix containing mercury in the dental region to be restored, whereby mercury released from the amalgam mix binds to the mercury-absorbing palladium composition.

8. The method of claim 7 wherein said amalgam mix comprises a silver alloy-mercury plastic amalgam mix.

9. The method of claim 7 wherein the mercury-absorbing palladium composition comprises at least approximately 50% by weight of palladium.

10. The method of claim 7 wherein the remaining portion of the mercury-absorbing palladium composition consists of materials selected from the group of copper, platinum, indium, zinc, and gold.

11. The method of claim 7 wherein the mercury-absorbing metal composition comprises a metal powder having a particle size of approximately between 0.1 $\mu$m and 50 $\mu$m.

12. The method of claim 7 wherein the mercury-absorbing metal composition comprises a metal foil having a thickness of approximately between 5 $\mu$m and 13 $\mu$m.

13. A method of restoring a dental region in a living being, the method comprising the steps of:
- preparing a cavity region in the dental region to be restored;
- first installing a mercury-absorbing metal composition in the cavity region, by lining at least a portion of the cavity region with said mercury-absorbing metal composition, said mercury-absorbing metal composition being in the form of a thin foil containing palladium in combination with other metals selected from the group of gold, platinum, copper, silver, and indium;
- second installing an amalgam mix containing mercury in the cavity region, whereby mercury released from the amalgam mix binds to the mercury-absorbing metal composition.

14. The method of claim 13 wherein prior to performing said step of first installing there is provided the further step of lining the surface of the cavity region with a varnish.

15. The method of claim 13 wherein prior to performing said step of first installing there is provided the further step of lining the surface of the cavity region with a cement liner.

* * * * *